(12) United States Patent
Schwartz

(10) Patent No.: US 9,072,466 B2
(45) Date of Patent: Jul. 7, 2015

(54) LATENT PRINT DEVELOPMENT APPARATUS

(71) Applicant: Arnold Schwartz, Crompond, NY (US)

(72) Inventor: Arnold Schwartz, Crompond, NY (US)

(*) Notice: Subject to any disclaimer, the term of this patent is extended or adjusted under 35 U.S.C. 154(b) by 436 days.

(21) Appl. No.: 13/727,585

(22) Filed: Dec. 26, 2012

(65) Prior Publication Data

US 2014/0174365 A1  Jun. 26, 2014

Related U.S. Application Data

(62) Division of application No. 12/542,081, filed on Aug. 17, 2009, now Pat. No. 8,361,535.

(60) Provisional application No. 61/189,038, filed on Aug. 15, 2008.

(51) Int. Cl.
*C23C 16/00* (2006.01)
*A61B 5/117* (2006.01)
*A61B 5/103* (2006.01)
*F26B 13/10* (2006.01)

(52) U.S. Cl.
CPC ............... *A61B 5/117* (2013.01); *A61B 5/1172* (2013.01)

(58) Field of Classification Search
CPC ................ A61B 5/117; A61B 5/1172
USPC .................. 118/31.5; 427/1; 34/523
See application file for complete search history.

(56) References Cited

U.S. PATENT DOCUMENTS

| 5,348,759 A * | 9/1994 | Weaver et al. ............. 427/1 |
| 5,424,092 A * | 6/1995 | Weaver et al. ............. 427/1 |
| 7,487,739 B1 * | 2/2009 | Weaver et al. ........... 118/31.5 |

* cited by examiner

*Primary Examiner* — Keath Chen
(74) *Attorney, Agent, or Firm* — Ash Tankha; Lipton, Weinberger & Husick

(57) ABSTRACT

A kit, an apparatus, and method are provided for developing a latent print. The apparatus comprises a pellet comprising a substrate impregnated with a sublimation compound, a receptacle, an adapter, and an end cap. The receptacle is open at a first end and detachably connected to a heat source at a second end. The receptacle is designed to receive and accommodate the pellet through the first end of the receptacle. The adapter defines an annular space for transmission of heat from the heat source to the pellet. The first end of the adapter is connected to the second end of the receptacle and the second end of the adapter is in communication with the heat source. The end-cap comprising a mesh window in an annular space of the end-cap allows passage of the fumes released from the pellet through the open end of the end cap towards the latent print for development.

14 Claims, 10 Drawing Sheets

LATENT PRINT DEVELOPMENT APPARATUS

CROSS REFERENCE TO RELATED APPLICATIONS

This application is a divisional of patent application Ser. No. 12/542,081, titled "Latent Print Development Apparatus", filed Aug. 17, 2009 in the United States Patent and Trademark Office which claims the benefit of provisional patent application No. 61/189,038 titled "A Proprietary Cartridge Design For A Fuming Wand, For Use In Forensic Latent Print Development", filed on Aug. 15, 2008 in the United States Patent and Trademark Office.

BACKGROUND

The apparatus and method disclosed herein, in general, relates to a latent print development apparatus. More particularly, the apparatus and method disclosed herein relates to using a pellet comprising a substrate impregnated with a sublimation compound in a latent print development apparatus. The substrate comprises stainless steel wool, fibrous and porous materials, cotton gauze, flax, etc. The sublimation compound comprises compounds such cyanoacrylate, etc.

Cyanoacrylate is used in forensic science for capturing latent prints, for example, fingerprints on non-porous surfaces. When cyanoacrylate is heated beyond its sublimation temperature, cyanoacrylate sublimates into a white vapor that adheres to the residues of a latent print to reveal the print's topography, outline, ridges, etc.

Former devices and techniques for developing latent finger prints produced fairly good results. However, these devices used techniques that were time consuming, taking several hours, and had to be performed in enclosed spaces. In the late 1990s, a different approach was introduced that allows the devices to be used both indoors and outdoors. This approach also significantly reduced the print development time. However, this approach also has a few drawbacks, such as high operational cost, low ease of use, and the requirement to maintain a constant supply of liquid cyanoacrylate.

Another device for developing latent fingerprints uses a brass-housing for holding a porous substrate impregnated with cyanoacrylate. The brass-housing is a replaceable cartridge with a one-time use and is relatively expensive. The brass housing is attached to the exhaust port of a handheld butane torch by a friction fit. When the cyanoacrylate gets depleted during the fuming process, the brass housing has to be removed with pliers or tweezers, while the device is still hot, which poses a risk to the user and the surroundings. In addition to the expense incurred for replacing the brass housing when the cyanoacrylate gets depleted, there is a potential for damage when the brass housing is removed, both to the device and the user.

One recent technique incorporates a butane torch with a metal cartridge that connects directly to a clear plastic fuming housing. This technique uses a metal cartridge encapsulated within which is a marble sized-ball of steel wool positioned between two wire mesh screens. This design allows the user to recharge the steel wool ball, once the cured cyanoacrylate on the substrate is depleted. However, this design has its drawbacks, such as, managing multiple components and additional clean ups, handling of additional cyanoacrylate carried in a small bottle for recharging the steel wool ball, and requiring additional downtime during each recharge, and waiting for the cyanoacrylate to cure.

Therefore, there is a need for an apparatus and method for developing a latent print that reduces the operational cost, provides ease of use, and does not require any significant downtime between applications.

BRIEF DESCRIPTION OF THE DRAWINGS

The following detailed description of the invention is better understood when read in conjunction with the appended drawings. For the purpose of illustrating the invention, exemplary constructions of the invention are shown in the drawings. However, the invention is not limited to the specific methods and instrumentalities disclosed herein.

DETAILED DESCRIPTION OF THE INVENTION

Figure 1:
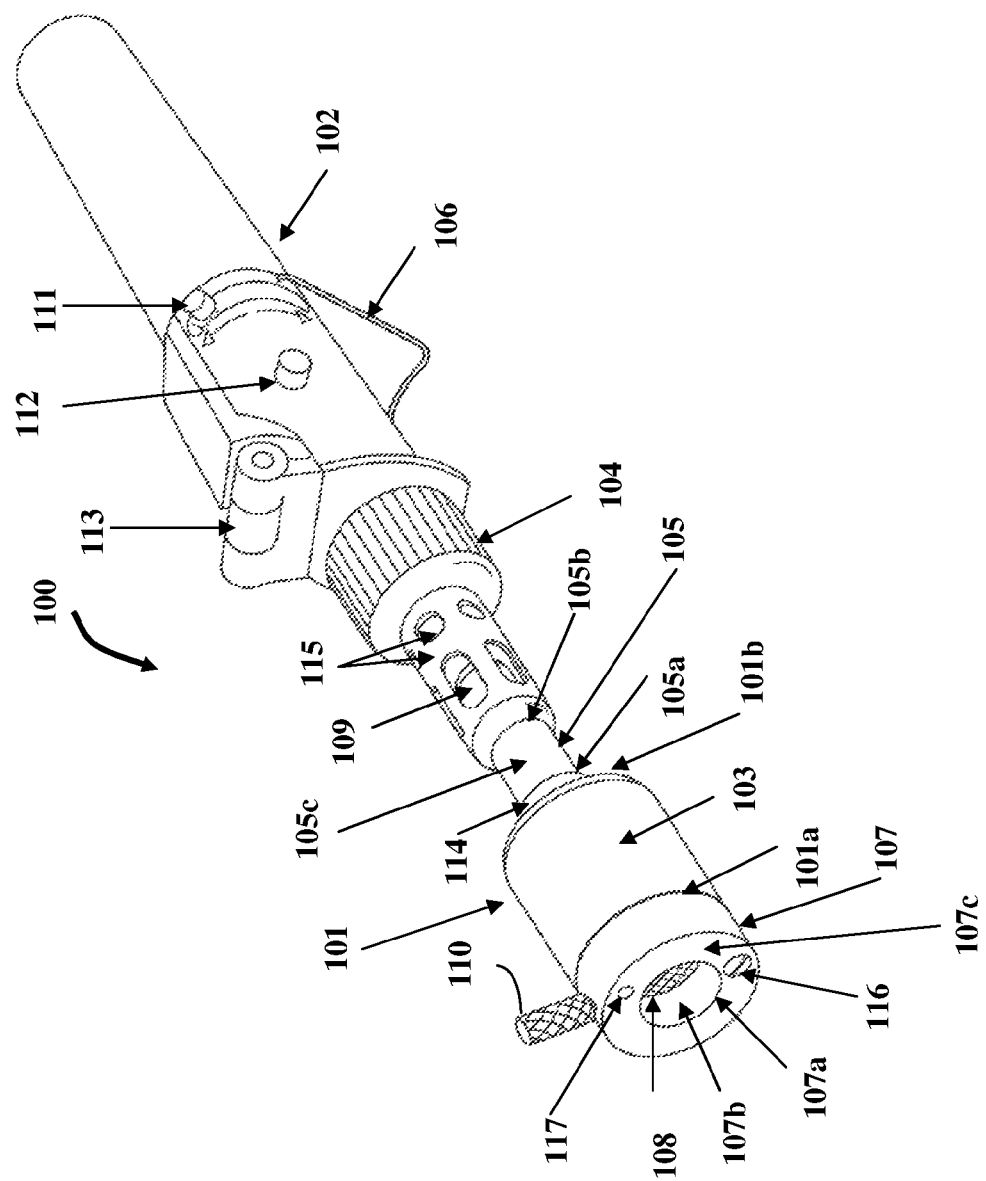
FIG. 1 illustrates a side perspective view of a latent print development apparatus.

An apparatus 100 is provided for developing a latent print. FIG. 1 illustrates a side perspective view of a latent print development apparatus 100. The latent print development apparatus 100 herein referred to as the "apparatus" comprises a pellet 202, a generally cylindrical receptacle 101 that defines an annular inner space 101c with a first end 101a and a second end 101b for housing the removable pellet 202, a generally cylindrical adapter 105 that defines an annular space 105c, and a generally cylindrical end-cap 107 designed to mate with and close the first end 101a of the receptacle 101. The pellet 202 as exemplarily illustrated in FIG. 2 comprises a substrate impregnated with a sublimation compound. The receptacle 101 is open to the environment at the first end 101a through an annular opening 107a in the end-cap 107, and is detachably connected to a heat source 102 through the second end 101b. The receptacle 101 is designed to receive and accommodate the pellet 202 through the first end 101a of the receptacle 101. The adapter 105 shown in FIG. 3 defines an annular space 105c for transmission of heat from the heat source 102 to the pellet 202. The adapter 105 has a first end 105a and a second end 105b. The first end 105a of the adapter 105 is connected to the second end 101b of the receptacle 101 and the second end 105b of the adapter 105 is in communication with the heat source 102, for example a butane torch. The first end 107c of the end cap 107 has an annular opening 107a. The end-cap 107 is removably attached to the first end 101a of the receptacle 101, for example by a pivotal connection. The annular space 107b within the end-cap is in fluid communication with the annular space 101c of the receptacle 101. The end-cap 107 comprising a mesh window 108 in the annular space 107b of the end-cap 107 allows fumes released from the pellet 202 to be directed through the annular opening 107a of the end-cap 107 towards the latent print to enable the development of the latent print.

The receptacle 101 of the apparatus 100 is an open ended generally cylindrical enclosure 103. The receptacle 101 is designed to receive and accommodate a removable pellet 202, as exemplarily illustrated in FIG. 2. The pellet 202 comprises a sintered substrate impregnated with a sublimation compound, for example, a cyanoacrylate polymer. The pellet 202 is shaped and impregnated with the sublimation compound independent of and external to the receptacle 101. In an embodiment, the pellet 202 is in the shape of a disc impregnated with the sublimation compound. The pellet 202 is introduced into the annular inner space 101c of the receptacle 101 through the first end 101a of the receptacle 101 and releases fumes on application of heat from the heat source 102. The pellet 202 is dropped into the opening 101c through the first end 101a of the receptacle 101. The diameter of the cylindrical pellet 202 is slightly larger than the opening at the second end 101b, so that the pellet 202 remains securely held inside the annular inner space 101c of the receptacle 101 throughout the fuming process. "Fuming process" as used herein refers to the passage of heated air over the cured pellet 202 to produce vapors of the sublimation compound that are directed towards the latent prints. Also, "cured pellet" as used herein refers to the pellet 202 saturated with the sublimation compound.

Figure 2:
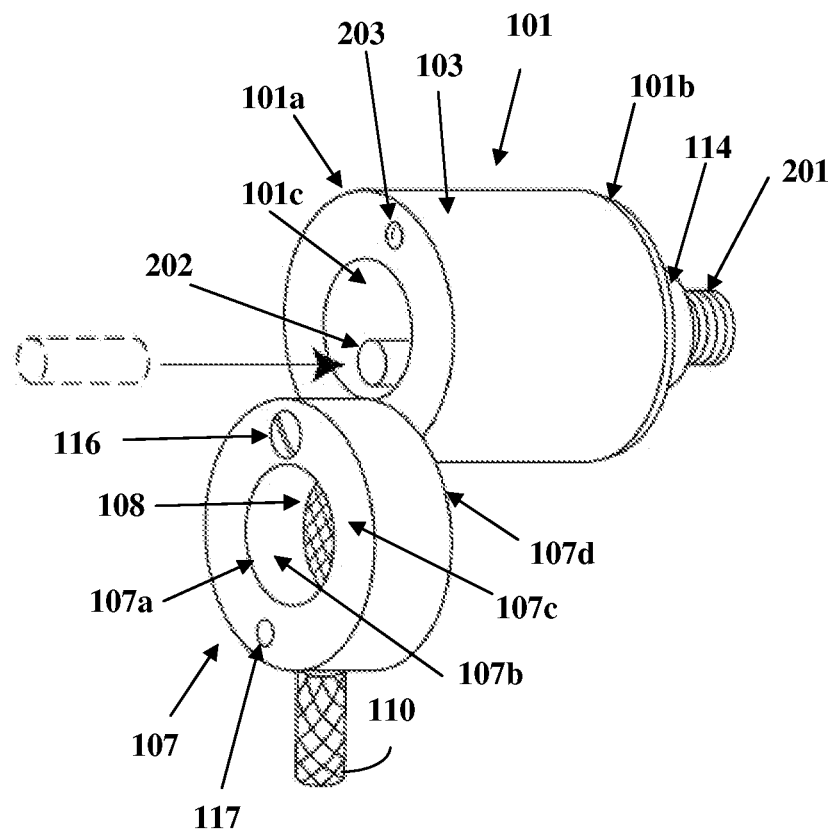
FIG. 2 exemplarily illustrates a side perspective view of a receptacle and an end cap of the latent print development apparatus.
Figure 3:
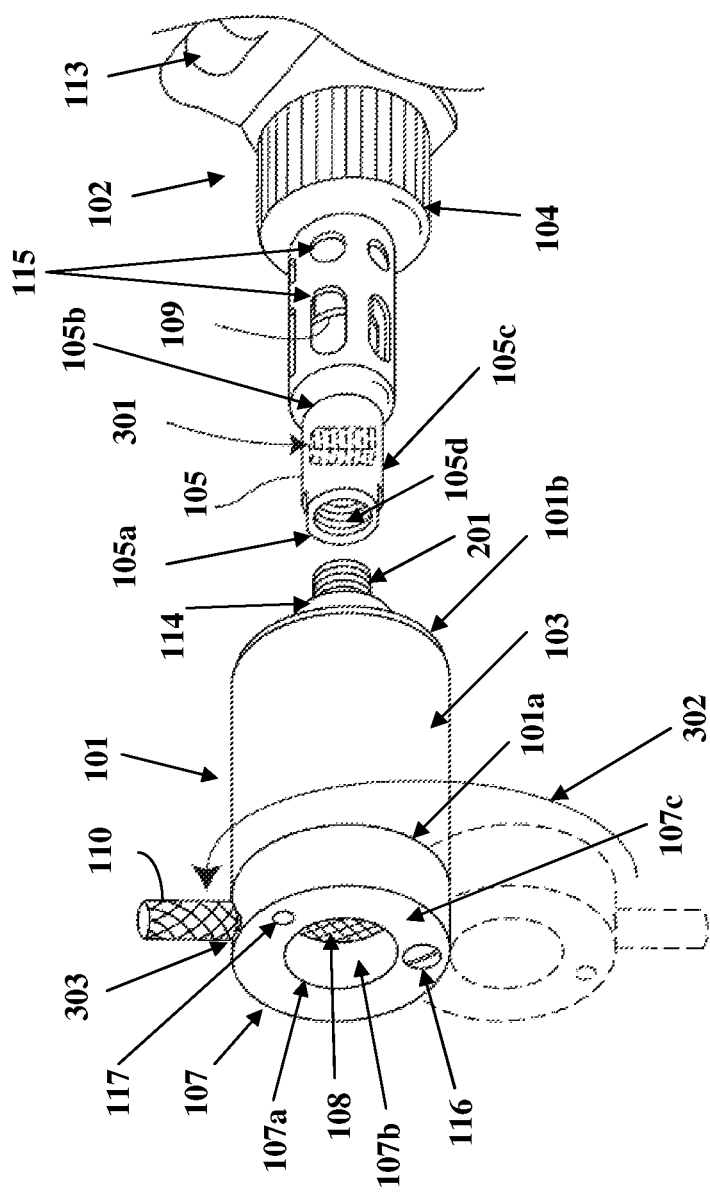
FIG. 3 exemplarily illustrates an exploded side perspective view of the latent print development apparatus showing the receptacle, a heat diffuser, a metal adapter, and a section of a heat source.

The end-cap 107 detachably connects to the first end 101a of the receptacle 101, for example, by a pivoting movement 302 of the end-cap 107 about a pivoting point 116 on the first end 101a of the receptacle 101, as exemplarily illustrated in FIG. 3. The end-cap 107 is a generally cylindrical housing defining an annular space 107b with an annular opening 107a as illustrated in FIGS. 1-9 for allowing the fumes generated to be exhausted through the annular opening 107a and directed towards the latent print. A mesh window 108, made, for example, of woven brass wire or aluminum wire, in the end cap 107 is disposed within the annular space 107b in the end cap 107. The mesh window 108 traps non-sublimated particles and allows fumes released from the pellet 202 to be directed towards the latent prints.

FIG. 2 exemplarily illustrates a side perspective view of the receptacle 101 and end cap 107 of the apparatus 100. The receptacle 101 comprises a coaxial threaded extension 201 at the second end 101b of the receptacle 101 for attaching the receptacle 101 to the heat source 102. In an embodiment, the coaxial threaded extension 201 has a metal washer 114 for providing mechanical strength to the neck of the coaxial threaded extension 201.

FIG. 3 exemplarily illustrates an exploded side perspective view of the apparatus 100 showing the receptacle 101, a heat diffuser 301, the metal adapter 105, and a section of the heat source 102. The heat source 102 that is coupled to the receptacle 101 is, for example, a butane torch available from Porta-Lab™, and is specifically adapted for use in the apparatus 100 disclosed herein. The exhaust port 104 of the heat source 102 is attached to the metal adapter 105. The metal adapter 105 comprises a female internally threaded extension 105d. The coaxial threaded extension 201 at the second end 101b of the receptacle 101 engages the internally threaded extension 105d of the adapter 105 that is in communication with the heat source 102.

Figure 4:
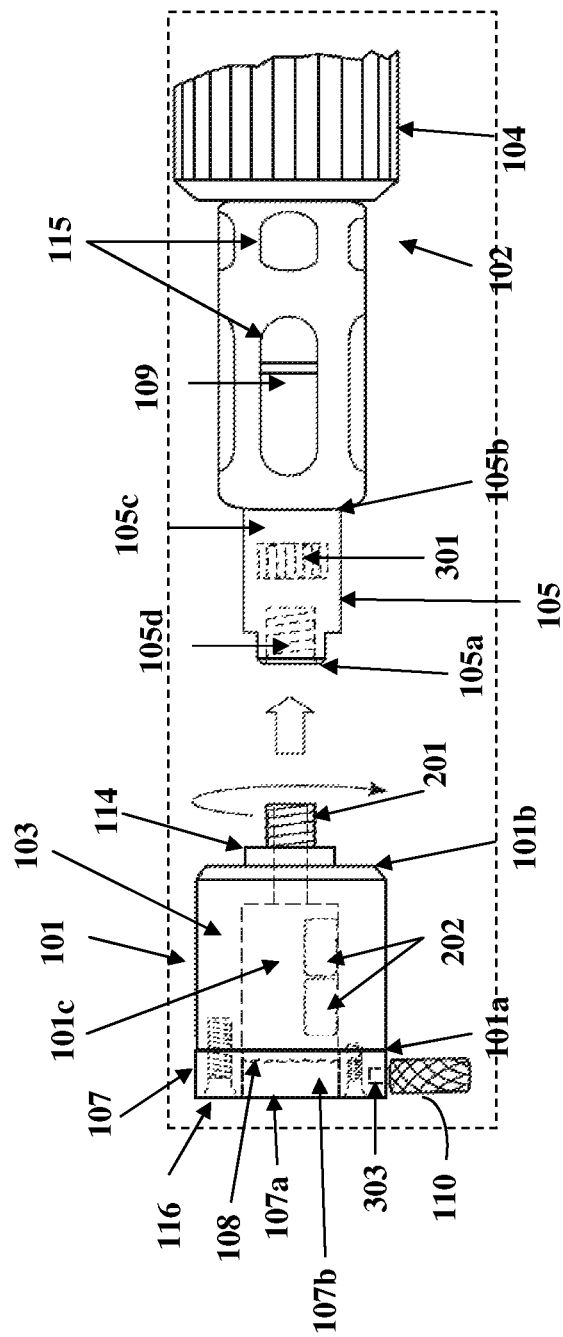
FIG. 4 exemplarily illustrates an exploded sectional orthogonal view of the latent print development apparatus showing the receptacle, the metal adapter, and a section of the heat source.

FIG. 4 exemplarily illustrates an exploded sectional orthogonal view of the apparatus 100 showing the receptacle 101 with the pellets 202, impregnated with the sublimation substance, positioned inside the annular inner space 101c, the end-cap 107 in the closed position, the metal adapter 105, and a section of the heat source 102 showing the metal adaptor 105 connected to the heat source 102. The coaxial threaded extension 201 of the receptacle 101 is fastened to the internally threaded extension 105d of the metal adapter 105, for connecting the receptacle 101 to the heat source 102, as exemplarily illustrated in FIG. 4. The apparatus 100 also comprises a support stand 106, for example, a wire frame stand, assembled to the butane torch 102 such that the resulting distribution of mass inclines the apparatus 100 towards a posterior end of the apparatus 100, as exemplarily illustrated in FIG. 1 and FIG. 9. The support stand 106 provides hands-free support for the apparatus 100 during the fuming operation. The apparatus 100 is set on the support stand 106 on the floor of a fuming chamber or inserted through a portal cover in a glass frame. The apparatus 100 may include a heat intensity control lever 111, a safety ignition switch 113, and a shut-off button 112, ergonomically located for user control when in operation, as exemplarily illustrated in FIG. 1 and FIG. 9.

Figure 5:
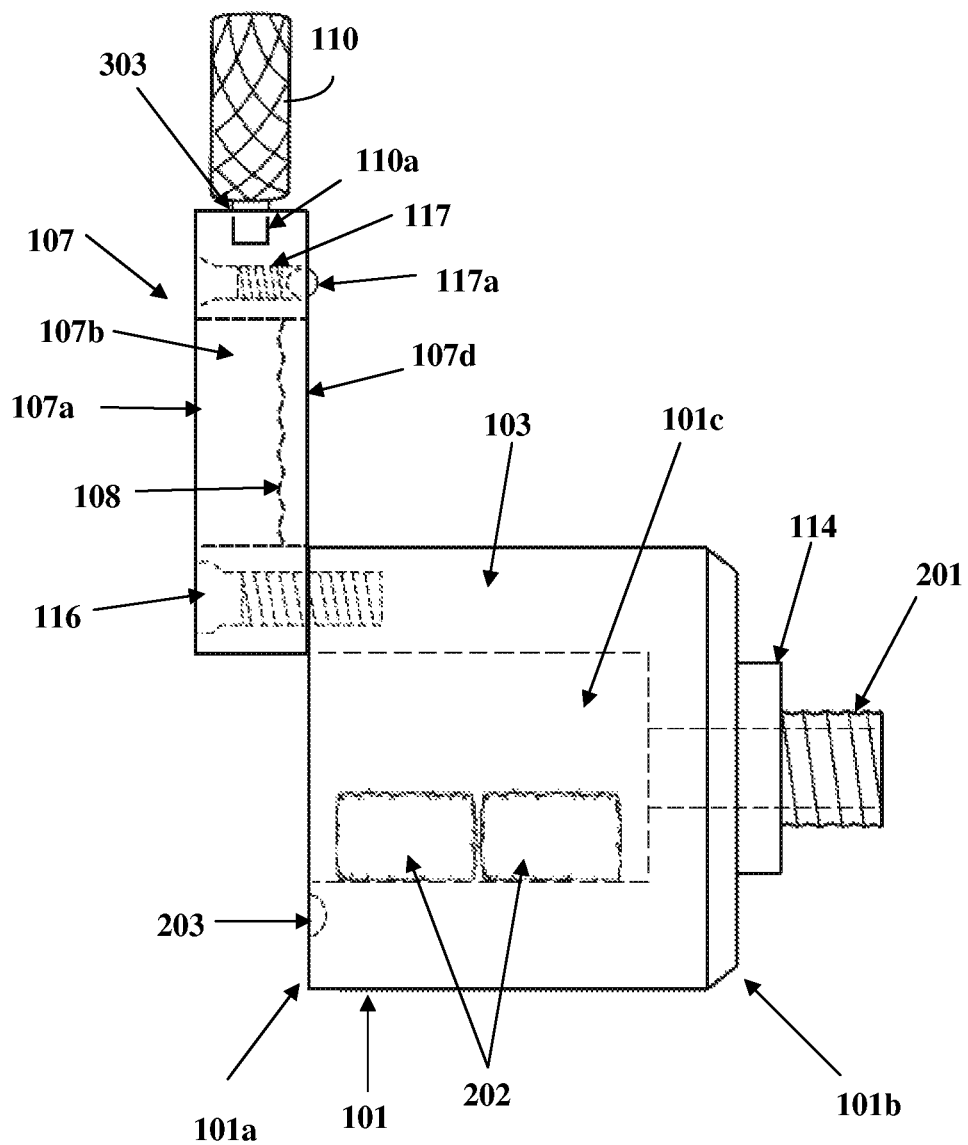
FIG. 5 exemplarily illustrates a sectional orthogonal view of the receptacle pivotally attached to the end cap.

FIG. 5 exemplarily illustrates a sectional orthogonal view of the receptacle 101 showing the pivotally attached end-cap 107 in the open position to allow the insertion or removal of the depleted pellet 202 from the annular space 101c in the receptacle 101. As exemplarily illustrated in FIG. 5, the receptacle 101 comprises a ball nose spring locking element 117 that is rigidly attached to the second end 107d of the end-cap 107. The ball nose spring locking element 117 comprises a ball nose 117a. The ball nose 117a of the ball nose spring locking element 117 engages a depression 203 on the first end 101a of the receptacle 101 to enable the end cap 107 to be locked to the first end 101a of the receptacle 101. The ball nose spring locking element 117 on the end cap 107 is located, for example, near a handle 110 of the end cap 107. In an embodiment, the ball nose spring locking element 117 also comprises a lock ring (not shown) to hold the ball nose 117a in place. In another embodiment, the ball nose spring locking element 117 is rigidly attached to the first end 101a of the receptacle 101, while the depression 203 is present on the end cap 107.

Figures 6A, 6B, 6C:
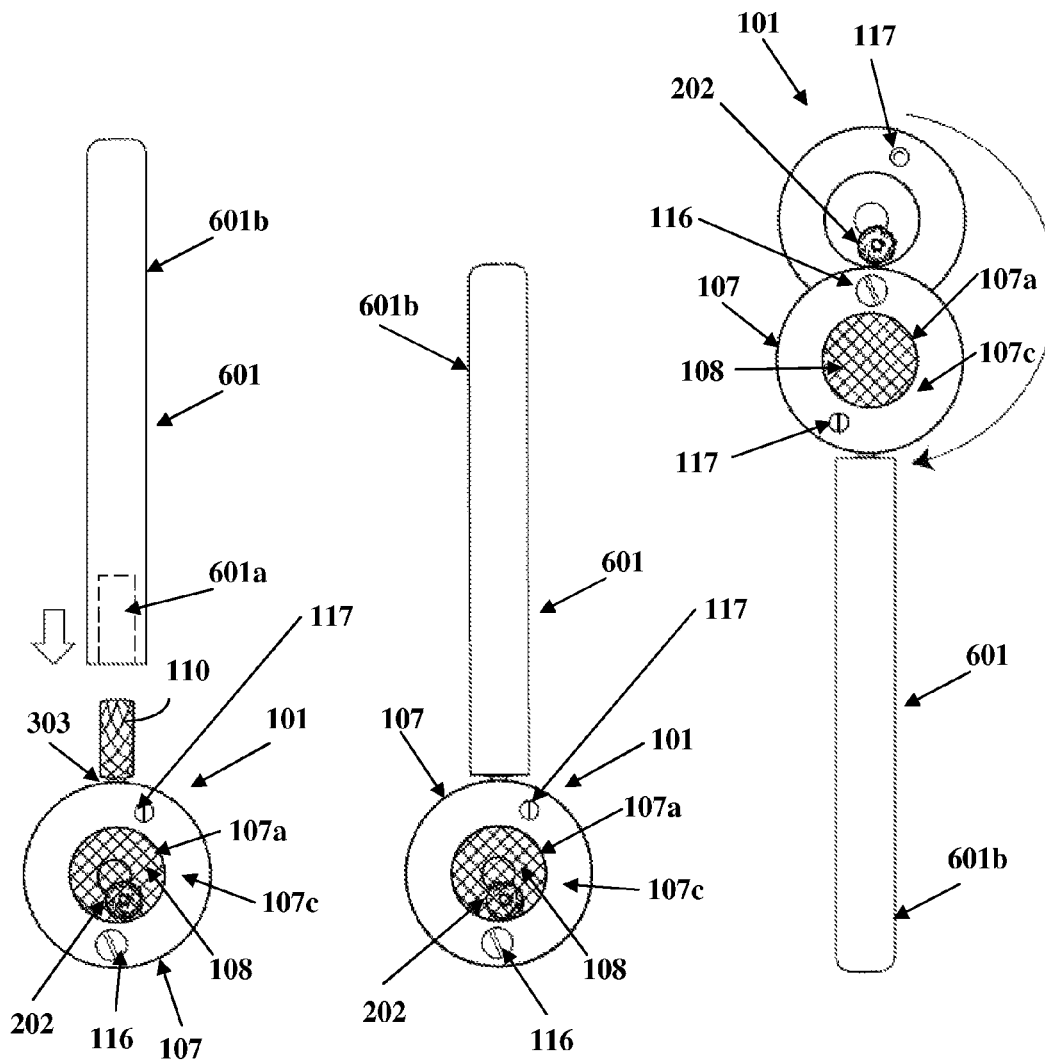
FIGS. 6A-6C exemplarily illustrate an embodiment of a removal mechanism of the latent print development apparatus.

The apparatus 100 further comprises a removal mechanism, for example, 110 or 601 as exemplarily illustrated in FIG. 6A. The removal mechanism 110 or 601 allows the user to remove the pellet 202 from the receptacle 101 when the sublimation compound from the pellet 202 is depleted and to insert a cured pellet 202, i.e. a pellet impregnated with the sublimation compound. The removal mechanism 110 or 601 enables the user to open the end-cap 107 and to eject the pellet 202 from the receptacle 101, even when the receptacle 101 is hot so as to allow the use of the fuming process to continue with minimal downtime. FIGS. 6A-6C exemplarily illustrate an embodiment of the removal mechanism 601. A handle 110 is rigidly attached to the end cap 107 at an attachment point 303 that is diametrically opposite to the pivoting point 116 on the first end 101a of the receptacle 101. The handle 110 opens the end-cap 107. The handle 110 is encased in a heat resistant material. The handle 110 doubles as a thumbscrew head that comprises a threaded shank extension 110a that is tightened into an internal threaded cavity in the end cap 107, as exemplarily illustrated in FIG. 5. The removal mechanism is for example an engaging tool. The engaging tool 601 engages with the handle 110 of the end-cap 107. The engaging tool 601 comprises a tool head 601a and an extended handle 601b encased in or made of a heat resistant material, for example, bakelite, polytetrafluoroethylene or Teflon®, etc., to enable the user to safely open the end-cap 107 and remove the pellet 202 depleted of the sublimation compound. The extended handle 601b is made of a heat resistant material.

Figure 7A:
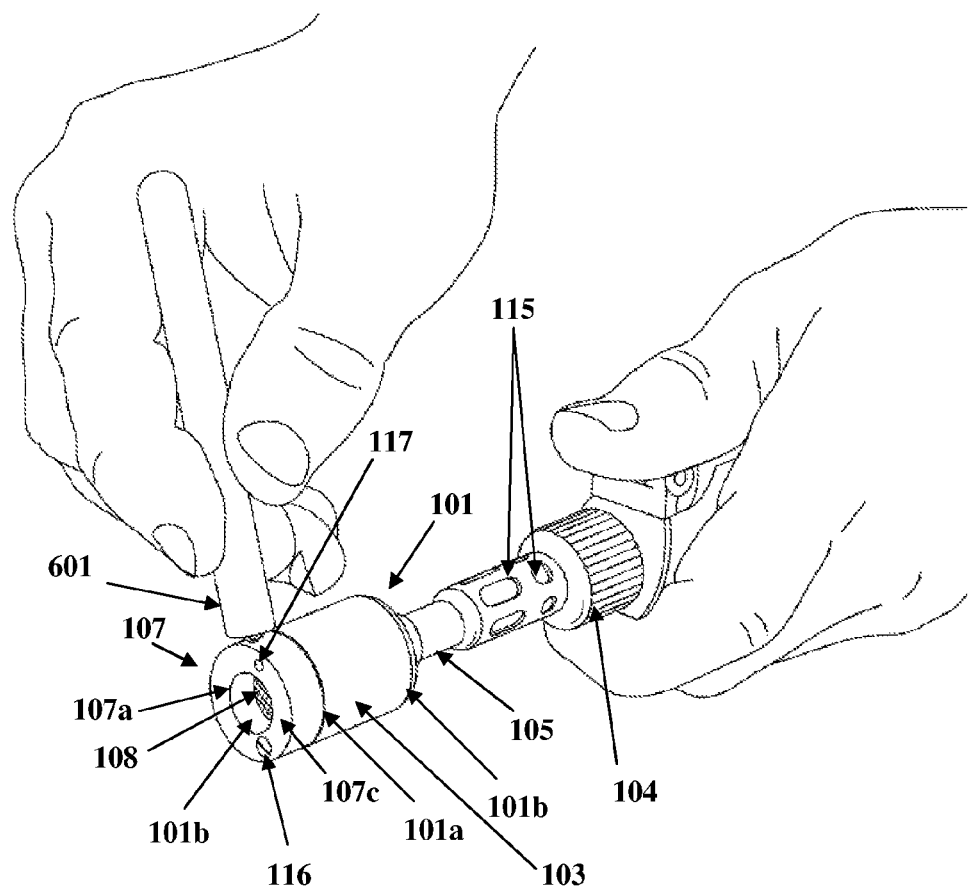
FIG. 7A exemplarily illustrates a user engaging a handle of the end cap in a closed position using an engaging tool.
Figure 7B:
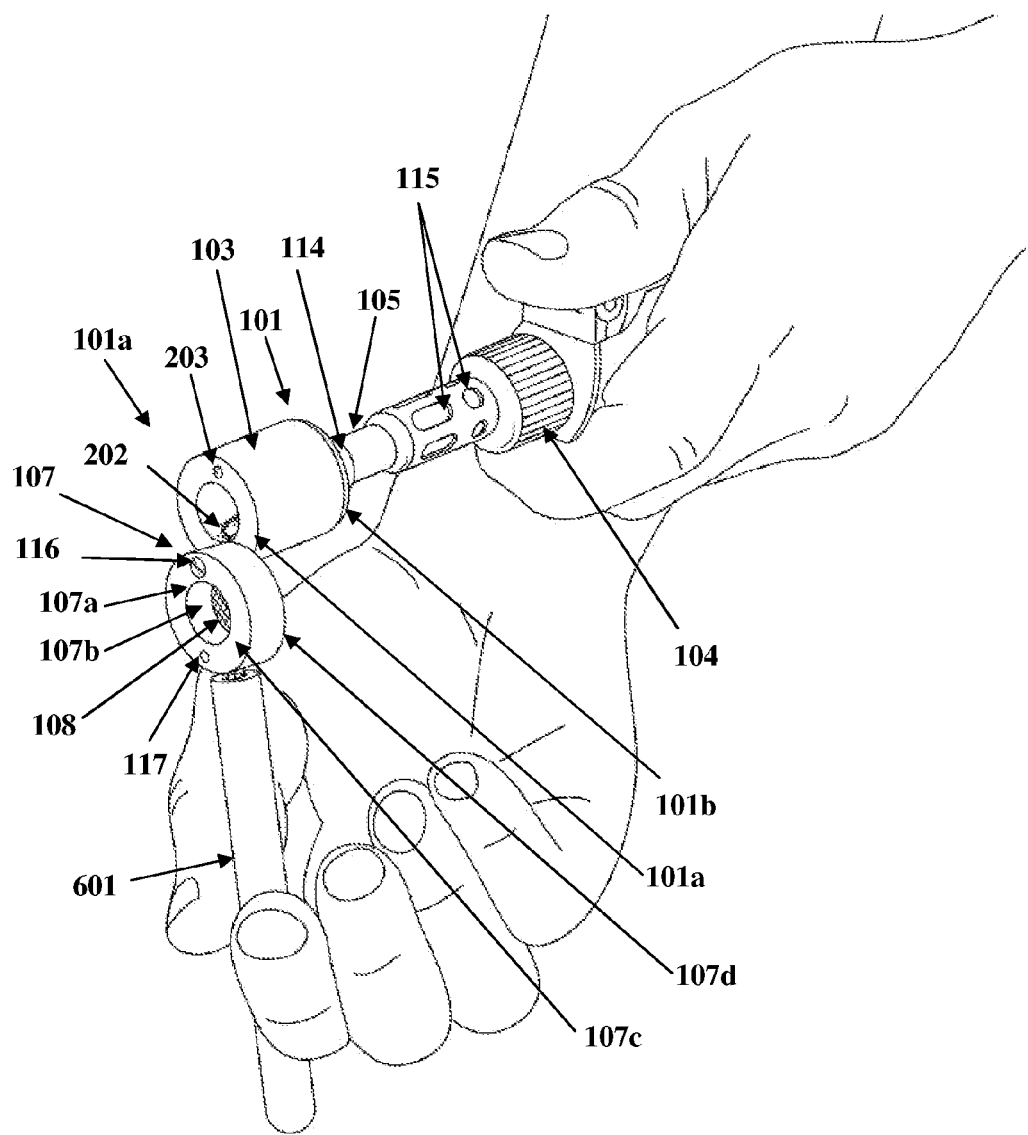
FIG. 7B exemplarily illustrates a user engaging a handle of the end cap in an open position using an engaging tool.

FIG. 6A illustrates a front exploded orthogonal view showing the receptacle 101, the end-cap 107, the handle 110, and the engaging tool 601. FIG. 6B illustrates a front orthogonal view showing the engaging tool 601 engaged to the handle 110 of the end-cap 107. FIG. 6C illustrates a front orthogonal view showing the engaging tool 601 engaged to the handle 110 of the end-cap 107, with the end-cap 107 swiveled to an open position. FIG. 7A exemplarily illustrates a user engaging a handle 110 of the end-cap 107 in a closed position using the engaging tool 601. FIG. 7B exemplarily illustrates a user engaging a handle 110 of the end cap 107 in an open position using the engaging tool 601. In an embodiment, the handle 110 is pre-extended in length and encased in or made of a heat resistant material. The extended handle 110 enables the user to safely open the end cap 107 and remove the pellet 202 depleted of the sublimation compound. Although the removal mechanism 110 or 601 has been described herein with reference to the handle 110 and the engaging tool 601, the removal mechanism 110 or 601 is not intended to be limited to the handle 110 and the engaging tool 601; but includes all functionally equivalent structures, for example, handgrips, knobs, pliers, extrinsic tools, etc.

To feed the pellets 202 into the receptacle 101 the following procedure is followed. The coaxial threaded extension 201 of the receptacle 101 is screwed to the internal thread 105d of the adapter 105. The handle 110 is connected to the end-cap 107, and the end-cover 107 is rotated to the open position 302. One or two sublimation pellets 202 are placed into the enclosure 101c. Holding the butane torch 102 with the receptacle 101 facing upward, the end-cap 107 is rotated to the closed position with the handle 110. The locking elements 117a and 203 will securely hold the end-cap 107 in the closed position. The pellets 202 will remain in the enclosure 103 and may move internally within the enclosure 103c without being expelled from the enclosure 103c as long as the end-cap 107 is in the closed position. The butane torch 102 is now ignited and the receptacle 101 pointed towards the evidence to be investigated. In about two minutes, the heat generated from the butane torch 102 as it passes through the adapter 105, will cause the pellets 202 to begin generating a fume of the sublimation compound. The sublimation fumes are exhausted through the meshing window 108 in the end-cap 107 and directed towards the evidence scene by holding the apparatus in an appropriate position. If a latent print is detected, the sublimation fumes will react with the latent print to develop a permanent image of the latent print within seconds. The sublimation fumes will cease to be generated within about two to four minutes after the fumes begin to be are generated with one sublimation pellet. The butane torch 102 is now turned off.

To remove the depleted pellets 202, the engaging tool 601 is inserted over the handle 110 attached to the end cap 107. The end cap 107 is then swiveled about the pivoting point 116 to open the receptacle 101. The butane torch 202 is inverted with the receptacle 101 facing downward. The depleted pellets 202 can now be discarded into a non-combustible container. If the depleted pellets 202 tend to stick inside the receptacle 101, a pointed object can be used to dislodge the depleted pellets 202 from the receptacle 101. One or two pellets 202 can now be introduced into the receptacle 101 and the end cap 107 can be closed using the engaging tool 601 and the fuming process can continue.

Figure 8:
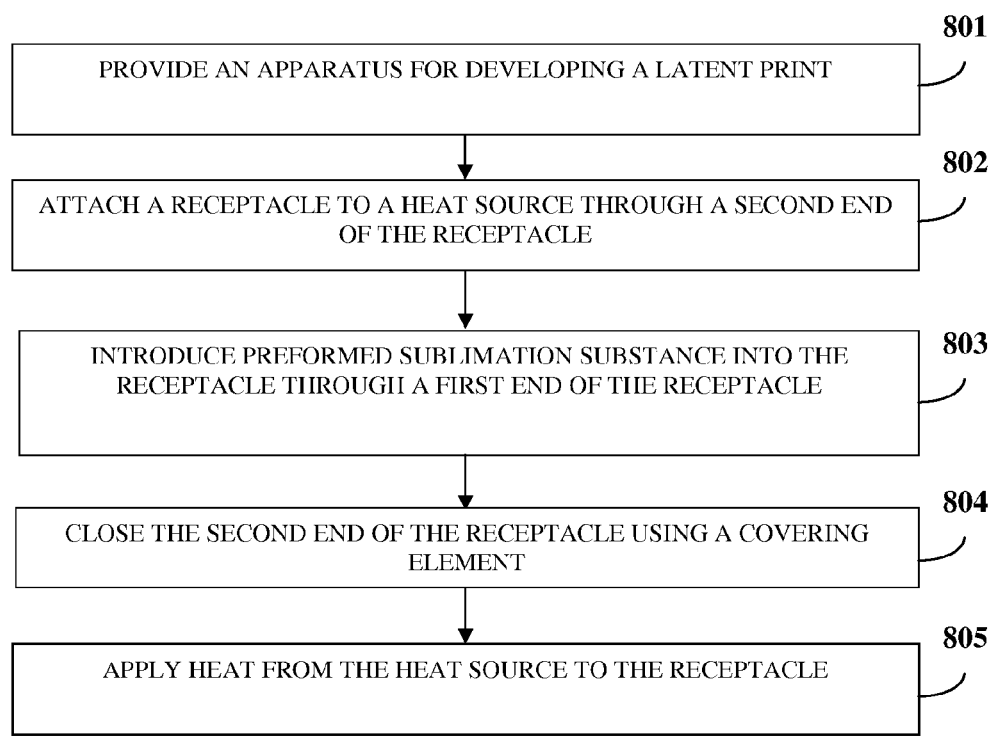
FIG. 8 illustrates a method of developing a latent print.
Figure 9:
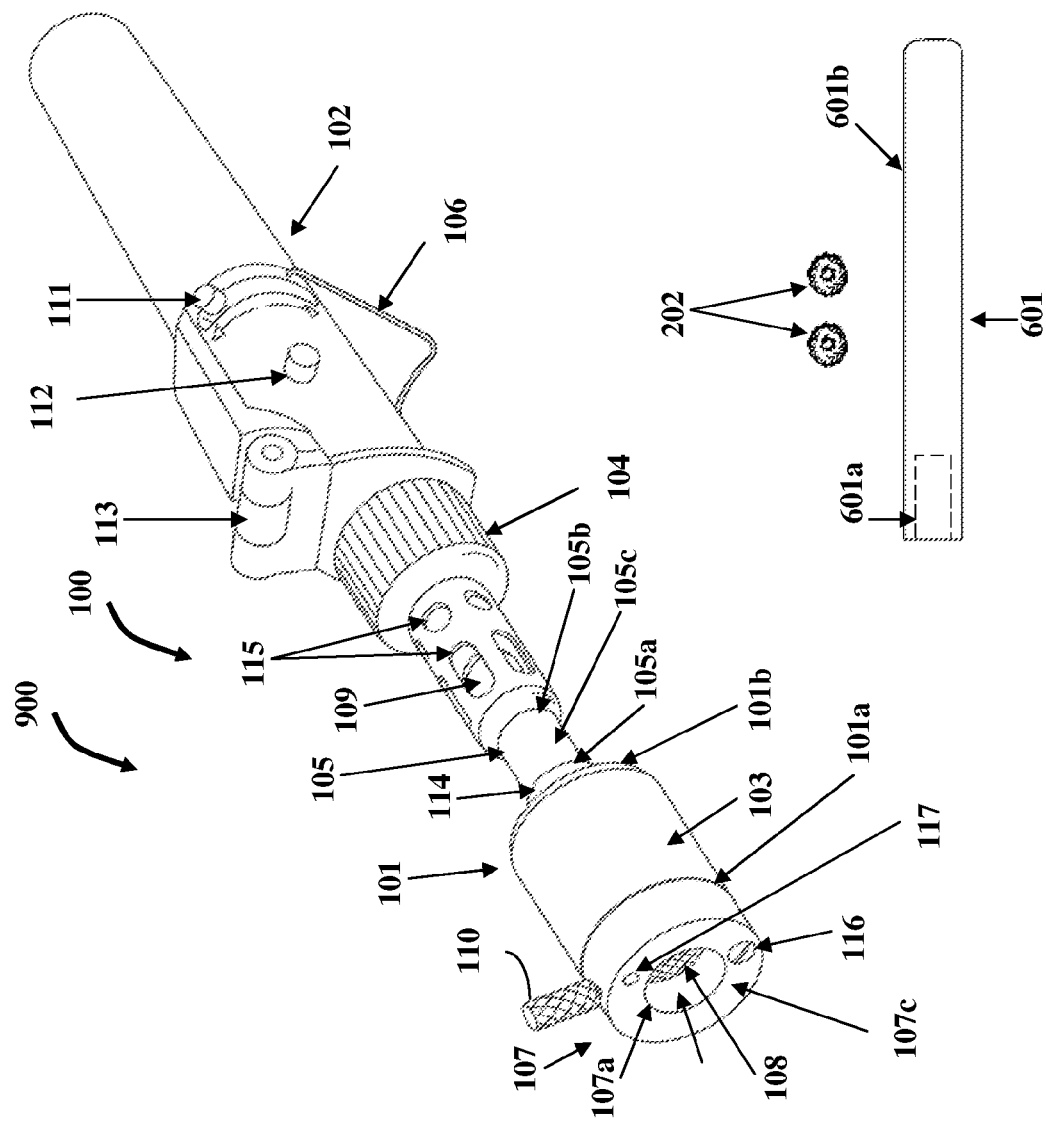
FIG. 9 exemplarily illustrates a portable latent print development kit.

FIG. 8 illustrates a method of developing a latent print. An apparatus 100 for developing a latent print, as illustrated and described in the detailed description of FIGS. 1-5, is provided 801. The receptacle 101 is attached 802 to the heat source 102 through the second end 101b of the receptacle 101. The receptacle 101 is attached to the heat source 102 by engaging a coaxial threaded extension 201 of the receptacle 101 to an internally threaded extension 105d of the adapter 105 in communication with the heat source 102. The receptacle 101 receives a pellet 202. The pellet 202 is introduced 803 into the receptacle 101 through the first end 101a of the receptacle 101. The first end 101a of the receptacle 101 is closed 804 with the end-cap 107. The heat source 102 supplies 805 heat to the receptacle 101 and the pellet 202 releases fumes through the open end 107a of the end-cap 107 towards the latent print via the mesh window 108 for development of the latent print. Heat applied from the heat source 102 passes through the heat diffuser 301 to the receptacle 101 via the adapter 105. The pellet 202 releases fumes on application of heat from the heat source 102. The fumes released through the mesh window 108 of the receptacle 101 enable the development of the latent print.

The end cap 107 is locked to the first end 101a of the receptacle 101 by engaging the ball nose 117a of the ball nose spring locking element 117 on the surface 107a of the end-cap 107 to the depression 203 on the first end 101a of the receptacle 101. The ball nose spring locking element 117 on the end-cap 107 is, for example, located near the handle 110. A removal mechanism, 110 or 601, is provided for removing the pellet 202 from the receptacle 101 when the pellet 202 has been depleted.

To start the fuming operation, the end cap 107 is swiveled into an open position and one or more pellets 202 impregnated with the sublimation compound are inserted into the receptacle 101. The end cap 107 is then swiveled 302 to a closed position. The fuel supply in the heat source 102, for example, the butane torch 102 is turned on, and a piezo-ignition ignites the butane torch 102. The flame from the butane torch 102 passes through a heat diffuser 301 built into the metal adapter 105 of the butane torch 102 as exemplarily illustrated in FIGS. 3-4. As the flame produced by the ignited butane gases reach the heat diffuser 301, the heat diffuser 301 absorbs the heat from the flames but does not allow the flames to cross the heat diffuser 301 and burn the substrate. The absorbed heat is propagated into the receptacle 101 as heated air. The ceramic material 109, seen through the windows 115 in the metal adapter 105, indicates that the butane gas has been ignited. When the butane torch 102 is burning, the ceramic material 109 glows bright red. The heated heat diffuser 301 drives the superheated air over the pellets 202 which causes the cured cyanoacrylate on the substrate to sublimate. The sublimation compound fumes produced are exhausted through the wire mesh window 108, and directed toward the latent fingerprint evidence to be developed. The white fumes or "bloom" produced reacts with the moisture or other chemical components of the latent print, and causes the latent print to develop within seconds.

The receptacle 101 is manufactured by a die casting process using, for example, aluminum due to its compatible properties for the intended applications for the apparatus 100 disclosed herein. The receptacle 101 comprises a generally cylindrical enclosure 103 with an annular inner space 101c and incorporates components, such as the pivotally mounted aluminum end cap 107 comprising a wire mesh window 108, the thumbscrew handle 110, and the ball nose spring locking element 117. The aluminum die cast enclosure 103 is, for example, 13 mm in inner diameter and holds up to two pellets 202 of the sublimation compound per application. A male coaxial threaded extension 201 with, for example, a 4.6 mm opening is designed to fasten to a female threaded extension 105d of the metal adapter 105 attached to the exhaust port 104 of the specially designed butane torch 102. The pellet 202, having a larger diameter, for example, 5 mm is thus held secure inside the annular inner space 101c of the receptacle 101.

Each pellet 202 can generate fumes for 2 to 4 minutes. When the pellet 202 is depleted of the cured cyanoacrylate impregnated on the substrate, the butane torch 102 is turned off. A removal mechanism 110 or 601, for example, the aluminum engaging tool 601 comprising a Teflon®-encased handle 601b, is provided that allows the user to safely open the heated enclosure 103 by engaging the handle 110 on the end cap 107, and remove the depleted pellet 202 from the receptacle 101 in minimal time. A new pellet 202 is dropped into the annular space 101c of the receptacle 101 and the end cap 107 is closed using the aluminum engaging tool 601. The butane torch 102 is now reignited, and the process for developing the latent print is continued, without any significant downtime.

The pellets 202 are manufactured using the following process. The process begins by cutting a strip of sintered stainless steel that is, for example, half an inch across, into smaller pieces. The resulting pieces are, for example, ⅝ of an inch in length and half an inch in width each. These pieces are then rolled into circular pellets 202. The sintered pellets 202 are then placed in a container into which a measured amount of the sublimation compound, for example cyanoacrylate is added to impregnate the pellet 202 and the impregnated pellets 202 are allowed to dry. The impregnated pellets 202 are packaged in plastic tubes containing pre specified units of impregnated pellets 202 for distribution. In an embodiment, stainless steel is sintered into fine fibers to create the stainless steel sheet that is used as the substrate. Regular steel wool when exposed to moisture over a period of time begins to oxidize or rust, resulting in a potential contaminant.

In an embodiment, the cyanoacrylate solution is treated with ultraviolet during its preparation. In an example, a solution is prepared by combining 15 grams of the solvent dichloromethane with 1 gram of Sievers' reagent. This provides a 5% Sievers solution (by weight) that is used as the UV enhancing component. A stainless steel wool pellet is placed into a polypropelene vial, and impregnated with 10 drops of cyanoacrylate. The stainless steel wool pellet is then sprayed with a curing agent or an accelerator to speed up the curing of the cyanoacrylate. A few drops of the Sievers solution is then added to the impregnated pellet 202, and allowed to evaporate. The resulting pellet 202 impregnated with the sublimation compound 202 is ready to be placed in the aluminum receptacle 101 of the apparatus 100, and heated above the sublimation point to produce fumes. The latent print that develops from the fumes is now radiated with a UV light source at about 395 nm wavelength. The developed latent print appears enhanced under a UV light source.

The primary application of the apparatus 100 is to provide a reliable method to detect and develop latent prints from evidence collected at a crime scene. A crime scene investigator uses the sublimation compound fumes produced by the apparatus 100 to attempt to develop latent prints, for example, fingerprints that may be present on non-porous surfaces of the crime scene evidence. The apparatus 100 is primarily designed for use at outdoor crime scenes, but can be used to develop a print from non-porous materials including metals, glass, varnished woods, plastics, and deceased bodies. The apparatus 100 can also be employed in a forensic laboratory to speed up latent print development in a "cyano" fuming chamber. Due to the portable nature of the apparatus 100, the evidence tested can be an individual item, inside an enclosed area, for example, an automobile, tent, car trunk, etc., in a forensic laboratory inside an enclosed fume hood, or under an exhaust hood.

In an embodiment, the method of applying heat from the heat source 102 is modified to exhibit a process used by federal investigation departments called "the microburst method for developing latent prints". The microburst method applies a very high temperature over a short period of time to the cured cyanoacrylate sublimate. This causes a rapid development of fumes and an almost instant curing of latent prints. The apparatus 100 disclosed herein can be adapted for the microburst method to produce "microburst prints" by removing the heat diffuser 301 from the metal adapter 105 at the neck of the butane torch 102. The open gas flame from the butane torch 102 is passed directly into the receptacle 101, exposing the cured pellets 202 of the sublimation compound to extremely high temperatures, and causing almost instant fuming and rapid development of the latent print.

The apparatus 100 disclosed herein may be included in a portable latent print development kit 900 with component parts capable of being assembled in the field. The portable latent print development kit 900 is exemplarily illustrated in FIG. 9. The portable latent print development kit 900 comprises a pellet 202, a generally cylindrical receptacle 101, a generally cylindrical adapter 105, a generally cylindrical end-cap 107, and a removal mechanism 110 or 601 as explained in the detailed description of FIGS. 1-5 and FIGS. 6A-6C. The portable latent print development kit 900 further comprises pre specified multiple units of the pellet 202 packaged in plastic containers. One or more units of the pellet 202 are introduced into the receptacle 101 through the second end 101b of the receptacle 101, and releases fumes on application of heat from the heat source 102. The portable latent print development kit 900 further comprises a removal mechanism 110 or 601 for removing the one or more units of the pellet 202 from the receptacle 101 when they are depleted.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

I claim:
1. An apparatus for developing a latent print, comprising:
a substrate system impregnated with a sublimation compound;
a generally cylindrical receptacle configured to define an annular space, said receptacle having a first end and a second end, said first end connected to an end cap, said second end having a coaxially threaded extension for detachably attaching said second end of said receptacle to a heat source via an adapter, wherein said first end of said receptacle is configured to receive and accommodate a pellet;

said adapter generally cylindrically shaped and configured to define an annular space for transmission of heat from said heat source to said substrate system via said adapter; and said end-cap generally cylindrical shaped, said end-cap having a pivot point defined at said first end of said receptacle, a handle fixedly attached to said end-cap at a position diametrically opposite to said pivot point, and an open end in communication with said first end of said receptacle, wherein said end-cap comprises a mesh window in an annular space of said end-cap to allow passage of said fumes released from said substrate system through said open end of said end cap towards said latent print.

whereby said fumes released through said mesh window of said receptacle enable said development of said latent print.

2. The apparatus of claim 1, wherein said substrate system impregnated with said sublimation compound is shaped in the form of a pellet.

3. The apparatus of claim 1, wherein said end cap is pivotally connected to said second end of said receptacle at a pivoting point on said second end of said receptacle.

4. The apparatus of claim 1, further comprising a removal mechanism for enabling removal of said substrate system from said receptacle.

5. The apparatus of claim 4, wherein said removal mechanism is a handle attached to said end cap at an attachment point that is diametrically opposite to a pivoting point on said second end of said receptacle to enable opening of said end cap, wherein said handle is made of a heat resistant material.

6. The apparatus of claim 5, further comprising an engaging tool for engaging said handle of said end cap, wherein said engaging tool comprises a tool head and an extended handle to enable opening of said end cap for removing said substrate system from said receptacle, wherein said extended handle is made of a heat resistant material.

7. The apparatus of claim 5, wherein said handle is pre-extended in length to enable safe opening of said end cap for removing said substrate system from said receptacle.

8. The apparatus of claim 1, further comprising a ball nose spring locking element comprising a ball nose rigidly attached to said end cap, wherein said ball nose of said ball nose spring locking element engages a depression on said second end of said receptacle to enable locking of said end cap to said second end of said receptacle, wherein said ball nose spring locking element on said end cap is located near a handle of said end cap.

9. The apparatus of claim 1, wherein said receptacle comprises a coaxial threaded extension located at said second end of said receptacle for attaching said receptacle to said heat source, wherein said coaxial threaded extension engages an internally threaded extension of said adapter in communication with said heat source.

10. A portable latent print development kit, comprising:
a substrate system impregnated with a sublimation compound;
a generally cylindrical receptacle configured to define an annular space, said receptacle having a first end and a second end, said first end connected to an end cap, said second end having a coaxially threaded extension for detachably attaching said second end of said receptacle to a heat source via an adapter, wherein said first end of said receptacle is configured to receive and accommodate a pellet;
said adapter generally cylindrically shaped and configured to define an annular space for transmission of heat from said heat source to said substrate system via said adapter;
said end-cap generally cylindrical shaped, said end-cap having a pivot point defined at said first end of said receptacle, a handle fixedly attached to said end-cap at a position diametrically opposite to said pivot point, and an open end in communication with said first end of said receptacle, wherein said end-cap comprises a mesh window in an annular space of said end-cap to allow passage of said fumes released from said substrate system through said open end of said end cap towards said latent print; and
a removal mechanism for removing said substrate system from said receptacle when said sublimation compound in said substrate system is depleted.

11. The portable latent print development kit of claim 10, wherein said substrate system impregnated with said sublimation compound is shaped in the form of a pellet.

12. The portable latent print development kit of claim 10, wherein said removal mechanism is a handle attached to said end cap at an attachment point that is diametrically opposite to a pivoting point on said first end of said receptacle to enable opening of said end cap, wherein said handle is made of a heat resistant material.

13. The portable latent print development kit of claim 12, further comprising an engaging tool for engaging said handle of said end cap, wherein said engaging tool comprises a tool head and an extended handle to enable opening of said end cap for removing said substrate system depleted of said sublimation compound from said receptacle, wherein said extended handle is made of a heat resistant material.

14. The portable latent print development kit of claim 10, wherein said removal mechanism is an extended handle rigidly attached to said end cap at an attachment point that is diametrically opposite to a pivoting point on said first end of said receptacle to enable said end cap to be opened for insertion or removal of said substrate system from said receptacle.

* * * * *